United States Patent [19]

Carrico et al.

[11] 4,213,893
[45] Jul. 22, 1980

[54] FLAVIN ADENINE DINUCLEOTIDE-LABELED CONJUGATES FOR USE IN SPECIFIC BINDING ASSAYS

[75] Inventors: Robert J. Carrico; Richard D. Johnson, both of Elkhart, Ind.

[73] Assignee: Miles Laboratories, Inc., Elkhart, Ind.

[21] Appl. No.: 950,858

[22] Filed: Oct. 12, 1978

Related U.S. Application Data

[63] Continuation-in-part of Ser. No. 917,962, Jun. 22, 1978.

[51] Int. Cl.$^2$ .................. C07C 103/52; C07G 7/00; A61K 37/00; C07H 19/16
[52] U.S. Cl. ........................ 260/112.5 R; 536/26; 424/177; 536/27
[58] Field of Search ................ 536/24, 27, 28, 26; 260/112.5 R

[56] References Cited

PUBLICATIONS

Hoard, D., and Ott, D., JACS, 87, 1785 (1965).
Guilford, H., et al., Chemica Scripta, 2, 165 (1972).
Trayer, I., et al., Biochem. J.,139, 609 (1974).
Asakura, H., et al., J. Radiat. Res., 15, 19 (1974).
Zomlicka, J., and Owens, J., J. Org. Chem., 42, 517 (1977).

*Primary Examiner*—Delbert R. Phillips
*Assistant Examiner*—Blondel Hazel
*Attorney, Agent, or Firm*—Andrew L. Klawitter

[57] ABSTRACT

Labeled conjugates of the formula:

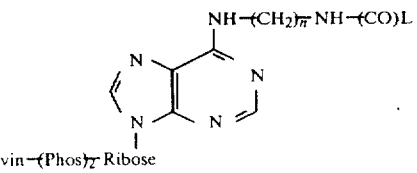

Riboflavin—(Phos)$_2$—Ribose wherein Riboflavin-(-Phos)$_2$Ribose represents the riboflavin-pyrophosphate-ribose residue in flavin adenine dinucleotide (FAD), n=2 through 6, and -(-CO)L is a specifically bindable ligand, or a binding analog thereof, and is preferably an iodothyronine such as thyroxine, bound through an amide bond; and intermediates produced in the synthesis of such FAD-labeled conjugates. The FAD-labeled conjugates are useful as labeled conjugates in specific binding assays for determining the ligand or a specific binding partner thereto in liquid media such as serum.

42 Claims, No Drawings

FLAVIN ADENINE DINUCLEOTIDE-LABELED CONJUGATES FOR USE IN SPECIFIC BINDING ASSAYS

CROSS-REFERENCE TO RELATED APPLICATION

This is a continuation-in-part of application Ser. No. 917,962, filed June 22, 1978.

BACKGROUND OF THE INVENTION

1. Field of the Invention

This invention relates to novel labeled conjugates for use in specific binding assays for ligands or their binding partners in a liquid medium. In particular, the invention relates to flavin adenine dinucleotide (FAD)-labeled conjugates for use in such assays, particularly for determining an iodothyronine such as thyroxine in serum. The invention further relates to intermediate compounds produced in the synthesis of the novel labeled conjugates.

The iodothyronines have the following general formula:

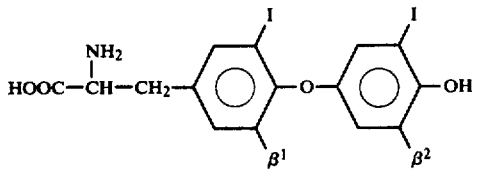

wherein $\beta^1$ and $\beta^2$ are, independently, hydrogen or iodine. The principal iodothyronines of clinical interest are listed in Table 1 below.

TABLE 1

| Iodothyronine | $\beta^1$ | $\beta^2$ |
|---|---|---|
| 3,5,3'5'-tetraiodothyronine (thyroxine; T-4) | iodine | iodine |
| 3,5,3'-triiodothyronine (liothyronine; T-3) | iodine | hydrogen |
| 3,3',5'-triiiodothyronine ("reverse" T-3) | hydrogen | iodine |
| 3,3'-diiodothyronine | hydrogen | hydrogen |

The quantitative determination of the concentration of the various iodothyronines, particularly the hormones T-3 and T-4, in serum and of the degree of saturation of the iodothyronine binding sites on the carrier protein thyroid binding globulin (TBG) are valuable aids in the diagnosis of thyroid disorders. Likewise, the determination of other components of body fluids including serum is useful in assessing the well-being of an individual. Examples of other substances of clinical interest are evident from the description below.

2. Brief Description of the Prior Art

Specific binding assay methods have undergone a technological evolution from the original competitive binding radioimmunoassay (RIA) in which a radioisotope-labeled antigen is made to compete with antigen from a test sample for binding to specific antibody. In the RIA technique, sample antigen is quantitated by measuring the proportion of radioactivity which becomes associated with the antibody by binding of the radiolabeled antigen (the bound-species of the labeled antigen) to the radioactivity that remains unassociated from antibody (the free-species) and then comparing that proportion to a standard curve. A comprehensive review of the RIA technique is provided by Skelly et al, Clin. Chem. 19: 146(1973). While by definition RIA is based on the binding of specific antibody with an antigen or hapten, radiolabeled binding assays have been developed based on other specific binding interactions, such as between hormones and their binding proteins.

From the radiolabeled binding assays have evolved nonradioisotopic binding assays employing labeling substances such as enzymes as described in U.S. Pat. Nos. 3,654,090 and 3,817,837. Recently further improved nonradioisotopic binding assays have been developed as described in German Offenlegungschriften Nos. 2,618,419 and 2,618,511, based on U.S. Ser. Nos. 667,982 and 667,996, filed on Mar. 18, 1976 and assigned to the present assignee, employing particularly unique labeling substances, including coenzymes, cyclic reactants, cleavable fluorescent enzyme substrates, and chemiluminescent molecules. Flavin adenine dinucleotide is mentioned as being useful as a coenzyme label since FAD functions as a coenzyme in useful monitoring reactions. In U.S. Patent application Ser. No. 917,961, filed June 22, 1978 and assigned to the present assignee, FAD is further described as useful in improved specific binding assays employing a prosthetic group as the label because FAD also functions as a prosthetic group in select biochemical systems.

Various methodologies exist for the determination of iodothyronine concentrations in serum. A significant advance in iodothyronine assays was the development of the competitive protein binding assay by Murphy and Pattee, J. Clin. Endocrinol. Metab. 24:187(1964) in which radiolabeled iodothyronine competes with serum iodothyronine for binding to TBG. The development of specific antiserum for the various iodothyronines permitted radioimmunoassays to be devised in which radiolabeled and serum iodothyronine compete for binding to antibodies rather than to TBG. In both the competitive protein binding assay and the radioimmunoassay for an iodothyronine, the radiolabeled material consists of the native iodothyronine in which one or more of the iodine atoms are replaced by a radioactive iodine isotope, usually $^{125}I$. The above-mentioned nonradioisotopic binding assays have offered even more advantageous methods for determining iodothyronines, particularly those methods described in U.S. Pat. Nos. 4,043,872 and 4,040,907 and most especially in OLS's 2,618,419 and 2,618,511 and U.S. Ser. No. 917,961 mentioned above.

SUMMARY OF THE INVENTION

Novel flavin adenine dinucleotide (FAD)-labeled conjugates have been devised for use in binding assays for determining ligands, or binding partners thereof, of analytical interest, such as the iodothyronines, and particularly for use in the assay referred to hereinbefore employing a prosthetic group label. The FAD-labeled conjugates have the general formula:

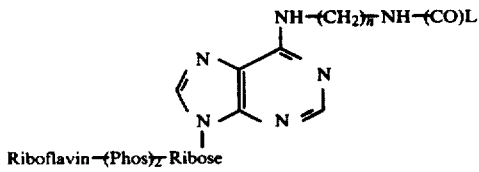

Riboflavin—(Phos)₂—Ribose wherein Riboflavin-(-Phos)₂Ribose represents the riboflavin-adenine Pyrophosphate-ribose residue in FAD; n=2 through 6, and preferably is 2 or 6; and —(CO)L is a specifically bindable ligand, or a specific binding analog thereof, and preferably is an iodothyronine such as thyroxine, bound through an amide bond.

The specifically bindable ligand or analog thereof in the present labeled conjugates, in terms of its chemical nature, usually is a protein, polypeptide, peptide, carbohydrate, glycoprotein, steroid, or other organic molecule for which a specific binding partner is obtainable. In functional terms, the ligand will usually be an antigen or an antibody thereto; a hapten or an antibody thereto; or a hormone, vitamin, or drug, or a receptor or binding substance therefor. Most commonly, the ligand is an immunologically-active polypeptide or protein of molecular weight between 1,000 and 4,000,000 such as an antigenic polypeptide or protein or an antibody; or is a hapten of molecular weight between 100 and 1,500.

FAD-labeled conjugates wherein the ligand therein is an iodothyronine are particularly useful in specific binding assays to determine the iodothyronine in liquid media such as serum and preferably have the general formula:

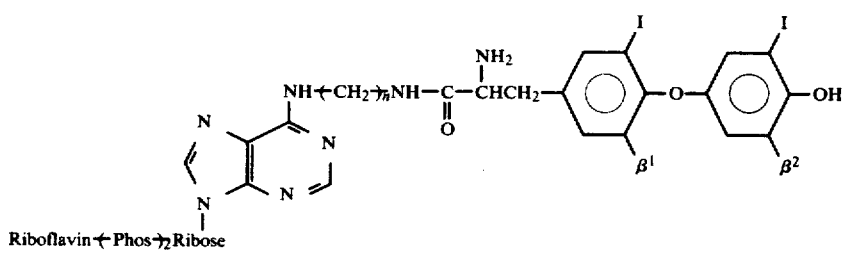

wherein Riboflavin-(-Phos-)₂Ribose represents the flavin mononucleotide-ribose residue in flavin adenine dinucleotide, n=2 through 6, and β¹ and β² are, independently, hydrogen or iodine.

The FAD-labeled conjugates are used in binding assays for the ligand or a specific binding partner therefor and are determined, i.e., monitored, for the purposes of the assay by measuring FAD activity, e.g., the coenzyme or prosthetic group activity of the labeled conjugate. Preferably the FAD-labeled conjugates are monitored by measuring holoenzyme activity generated upon combination of such conjugate with an apoenzyme that requires FAD to perform its catalytic function as described in detail in the above-mentioned U.S. Ser. No. 917,961.

The present FAD-labeled conjugates can be prepared by a variety of synthetic routes. Exemplary of such available synthetic routes is the following general reaction procedure:

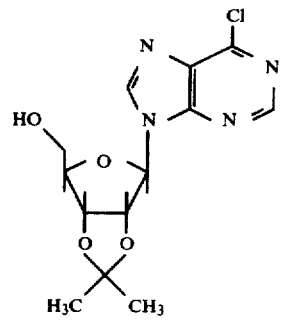

Reaction of 6-chloro-9-(2',3'-O-isopropylidine-β-D-ribofuranosyl) purine (1) [Hampton et al, *J. Am. Chem. Soc.* 83:150(1961)] with an α,ω-diaminoalkane selected from those listed in Table 2

TABLE 2

| n | α,ω-diaminoalkane |
|---|---|
| 2 | 1,2-diaminoethane |
| 3 | 1,3-diaminopropane |
| 4 | 1,4-diaminobutane |
| 5 | 1,5-diaminopentane |
| 6 | 1,6-diaminohexane | yields the intermediate 6-(ω-aminoalkyl)-9-(2',3'-O-isopropylidine-β-D-ribofuranosyl) purine (2).

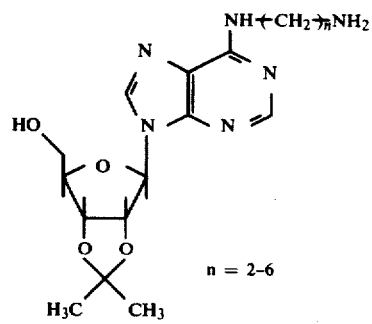

The amino-purine intermediate (2) is then linked by formation of a peptide or amide couple with either the ligand, where such contains a carboxylic acid function, or a binding analog of the ligand (e.g., a derivative of the ligand) which analog contains the desired carboxylic acid function, to form the ligand or analog substituted adenosine intermediate (3)

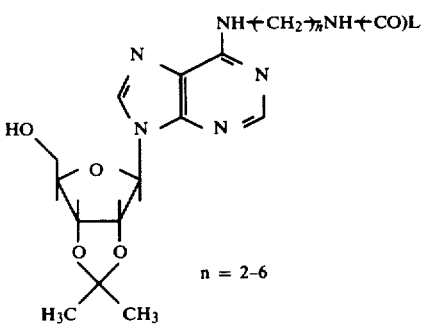

(3)

wherein —(CO)L is the ligand or analog thereof bound by an amide bond. Such condensation reactions can be accomplished by reacting the amino-purine intermediate (2) directly with the carboxylic acid-containing ligand or ligand analog using conventional peptide condensation reactions such as the carbodiimide reaction [*Science* 144:1344(1964)], the mixed anhydride reaction [Erlanger et al, *Methods In Immunology and Immunochemistry*, ed. Williams and Chase, Academic Press (New York 1967) p. 149], and the acid azide and active ester reactions [Kopple, *Peptides and Amino Acids*, W. A. Benjamin, Inc. (New York 1966)]. See also for a general review *Clin. Chem.* 22:726(1976).

It will be recognized, of course, that other well known methods are available for coupling the ligand or a derivative thereof to the amino-purine intermediate (2). In particular, conventional bifunctional coupling agents can be employed for coupling a ligand, or its derivative, containing a carboxylic acid or amino group to the amino-purine intermediate (2). For example, amine-amine coupling agents such as bis-isocyanates, bis-imidoesters, and glutaraldehyde [*Immunochem.* 6:53(1969)] can be used to couple a ligand or derivative containing an amino group to the amino-purine intermediate (2). Also, appropriate coupling reactions are well known for inserting a bridge group in coupling an amine (e.g., the amino-purine intermediate) to a carboxylic acid (e.g., the ligand or a derivative thereof). Coupling reactions of this type are thoroughly discussed in the literature, for instance in the above-mentioned Kopple monograph and in Lowe & Dean, *Affinity Chromatography*, John Wiley & Sons (New York 1974).

Such coupling techniques will be considered equivalents to the previously discussed peptide condensation reactions in preparing useful labeled conjugates. The choice of coupling technique will depend on the functionalities available in the ligand or analog thereof for coupling to the amino-purine intermediate (2) and on the length of bridging group desired. In all cases, for purposes of this disclosure, the resulting condensation product will comprise the amino-purine intermediate, which ultimately is converted to FAD, bound to the remaining portion of the product, or ultimately to the remaining portion of the FAD-labeled conjugate, through an amide bond. Such remaining portion of the condensation product, or conjugate, will be considered as a residue of a binding analog of the ligand, unless the ligand itself is directly coupled to the amino-purine intermediate (2). Thus, in this description and in the claims to follow, the abbreviation —(CO)L represents the ligand or a binding analog thereof coupled through an amide bond, wherein such analog can be a derivative of the ligand coupled by peptide condensation or can be the ligand or derivative thereof coupled through a bridging group inserted by coupling of the ligand or derivative with a bifunctional coupling agent.

It is evident that in coupling the ligand or derivative thereof to the amino-purine intermediate (2) it may be desirable to protect certain reactive groups in such ligand or derivative from participating in side reactions during coupling. Protection of reactive groups may also be desirable to prevent interfering reactions during the synthetic steps described below for completing the preparation of the FAD-labeled conjugate. Depending upon the specific ligand or derivative involved and the coupling technique chosen, the addition of protecting groups at the reactive sites on the ligand or derivative can be accomplished before or after the coupling to the amino-purine intermediate (2). One skilled in the art will have a wide variety of conventional blocking reactions from which to accomplish the desired protection of reactive groups such that the blocking group added can be readily removed in a subsequent synthetic step to yield the original ligand or derivative coupled to FAD.

For instance, where the ligand is an iodothyronine, it is preferably treated to protect the amine group prior to condensation or linkage with the amino-purine intermediate. The amine-protected iodothyronine intermediate has the formula:

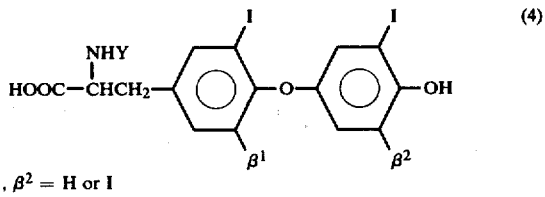

$\beta^1, \beta^2 = $ H or I wherein Y is an amine-protecting group. It will be recognized that protection of the amine group is a conventional procedure and the amine-protecting group can be selected from a wide variety of groups, including trifluoroacetyl, which is preferred, and the like, such as others of the acyl type (e.g., formyl, benzoyl, phthalyl, p-tosyl, aryl- and alkylphosphoryl, phenyl- and benzylsulfonyl, tritylsulfenyl, o-nitrophenylsulfenyl and o-nitrophenoxyacetyl), those of the alkyl type (e.g., trityl, benzyl and alkylidene) and those of the urethane type (e.g., carbobenzoxy, p-bromo-, p-chloro- and p-methoxycarbobenzoxy, tosyloxyalkyloxy-, cyclopentyloxy-, cyclohexyloxy-, t-butyloxy, 1,1-dimethylpropyloxy, 2-(p-biphenyl)-2-propyloxy- and benzylthiocarbonyl.

The substituted adenosine intermediates formed by condensation or linkage between the amino-purine intermediate (2) and the amine-protected iodothyronine intermediate (4) are of the formula (3) wherein —(CO)L is:

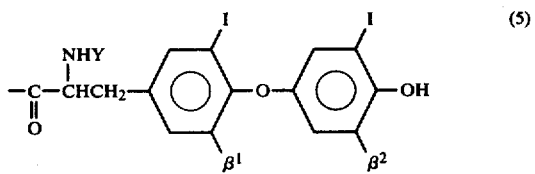

$\beta^1, \beta^2 = $ H or I wherein Y is an amine-protecting group as above.

Treatment of intermediate (3) with phosphorous oxychloride produces the phosphorylated ligand or analog substituted adenosine intermediate (6)

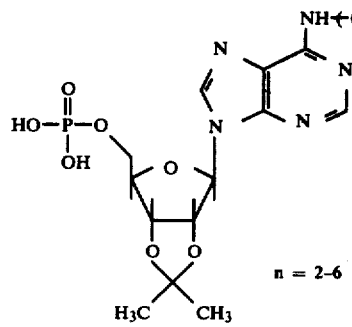

which upon hydrolysis yields the ligand or analog substituted 5'-adenylic acid intermediate (7).

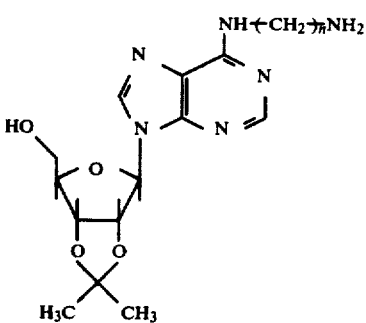

Condensation of riboflavin-5'-monophosphate with intermediate (7) activated to a phosphorimidazolidate by treatment with N,N'-carbonyldiimidazole yields FAD-labeled conjugates (8).

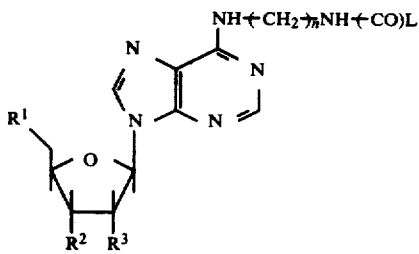

In the preferred embodiment wherein the ligand is an iodothyronine, and thus ─(CO)L is represented by formula (5) above, the resulting FAD-iodothyronine conjugates are of the formula:

correspond to formula A below and the intermediates (3, 6 and 7) correspond to formula B below]:

formula A

NH─(CH$_2$)$_n$NH$_2$ (structure shown)

wherein n=2 through 6; and formula B

NH─(CH$_2$)$_n$NH─(CO)L (structure shown)

wherein ─(CO)L is a specifically bindable ligand, or a binding analog thereto, and preferably is of formula (5), bound through an amide bond; n=2 through 6; $\beta^1$ and $\beta^2$ are, independently, hydrogen or iodine; R$^1$ is ─OH or $$-O-\overset{O}{\underset{OH}{\overset{\|}{P}}}-OH$$

when R$^2$ and R$^3$ together form the group (9)

(structure shown with NHY, CHCH$_2$, iodines, $\beta^1$, $\beta^2$, OH)

Riboflavin─(Phos)$_2$Ribose
$\beta^1$, $\beta^2$ = H or I
n = 2-6 wherein Y is an amine-protecting group or, upon conventional treatment for removal of such protecting group, Y is hydrogen.

As illustrated above, the novel intermediate compounds (2, 3, 6 and 7) produced in the course of synthesizing the FAD-labeled conjugates have the following general formulae [the amino-purine intermediates (2)

or R$^1$ is (structure with two iodines, O, O, C(CH$_3$)$_2$)

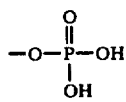

when R² and R³ are —OH.

As stated hereinabove, the ligand which is comprised in the labeled conjugate or whose binding analog is comprised in the labeled conjugate is in most circumstances an immunologically-active polypeptide or protein of molecular weight between 1,000 and 4,000,000, such as an antigenic polypeptide or protein or an antibody, or is a hapten of molecular weight between 100 and 1,500. Various methods for coupling such ligands or analogs thereof to the amino-purine intermediate (2) through an amide bond in the synthesis of the present FAD-labeled conjugate will now be presented.

Polypeptides and Proteins

Representative of specifically bindable protein ligands are antibodies in general, particularly those of the IgG, IgE, IgM and IgA classes, for example hepatitis antibodies; and antigenic proteins such as insulin, chorionic gonadotropin (e.g., HCG), carcinoembryonic antigen (CEA), myoglobin, hemoglobin, follicle stimulating hormone, human growth hormone, thyroid stimulating hormone (TSH), human placental lactogen, thyroxine binding globulin (TBG), instrinsic factor, transcobalamin, enzymes such as alkaline phosphatase and lactic dehydrogenase, and hepatitis-associated antigens such as hepatitis B surface antigen (HB$_s$Ag), hepatitis B e antigen (HB$_e$Ag) and hepatitis B core antigen (HB$_c$Ag). Representative of polypeptide ligands are angiotensin I and II, C-peptide, oxytocin, vasopressin, neurophysin, gastrin, secretin, and glucagon.

Since, as peptides, ligands of this general category possess numerous available carboxylic acid and amino groups, coupling to the amino-purine intermediate (2) can proceed according to conventional peptide condensation reactions such the carbodiimide reaction, the mixed anhydride reaction, and so forth as described hereinabove, or by the use of conventional bifunctional reagents capable of coupling carboxylic acid or amino functions to the amino group in the amino-purine intermediates (2) as likewise described above. General references concerning the coupling of proteins to primary amines or carboxylic acids are mentioned in detail above.

Haptens

Haptens, as a class, offer a wide variety of organic substances which evoke an immunochemical response in a host animal only when injected in the form of an immunogen conjugate comprising the hapten coupled to a carrier molecule, almost always a protein such as albumin. The coupling reactions for forming the immunogen conjugates are well developed in the art and in general comprise the coupling of a carboxylic acid ligand or a carboxylic acid derivative of the ligand to available amino groups on the protein carrier by formation of an amide bond. Such well known coupling reactions are directly analogous to the present formation of labeled conjugates by coupling carboxylic acid ligands or binding analogs to the amino-purine intermediate (2).

Hapten ligands which themselves contain carboxylic acid functions, and which thereby can be coupled directly to the amino-purine intermediate (2), include the iodothyronine hormones such as thyroxine and liothyronine, as well as other materials such as biotin, valproic acid, folic acid and certain prostaglandins. Following are representative synthetic routes for preparing carboxylic acid binding analogs of hapten ligands which themselves do not contain an available carboxylic acid function whereby such analogs can be coupled to the amino-purine intermediate (2) by the aforementioned peptide condensation reactions or bifunctional coupling agent reactions (in the structural formulae below, n represents an integer, usually 1 through 6, and Me represents methyl).

Carbamazepine

Dibenz[b,f]azepine is treated sequentially with phosgene, an ω-aminoalkanol, and Jones reagent (chromium trioxide in sulfuric acid) according to the method of Singh, U.S. Pat. No. 4,058,511 to yield the following series of carboxylic acids:

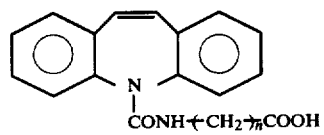

Quinidine

Following the method of Cook et al, *Pharmacologist* 17:219(1975), quinidine is demethylated and treated with 5-bromovalerate followed by acid hydrolysis to yield a suitable carboxylic acid derivative.

Digoxin and Digitoxin

The aglycone of the cardiac glycoside is treated with succinic anhydride and pyridine according to the method of Oliver et al, *J. Clin. Invest.* 47:1035(1968) to yield the following:

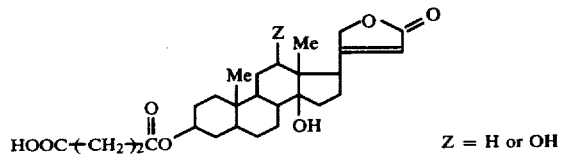

Z = H or OH

Theophylline

Following the method of Cook et al, *Res. Comm. Chem. Path. Pharm.* 13:497(1976), 4,5-diamino-1,3-dimethylpyrimidine-2,6-dione is heated with glutaric anhydride to yield the following:

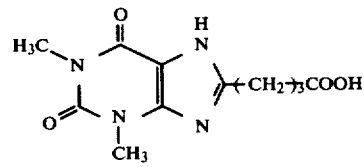

Phenobarbital and Primidone

Sodium phenobarbital is heated with methyl 5-bromovalerate and the product hydrolyzed to the corresponding acid derivative of phenobarbital [Cook et al, *Quantitative Analytic Studies in Epilepsy*, ed. Kelleway and Peterson, Raven Press (New York 1976) pp. 39–58]:

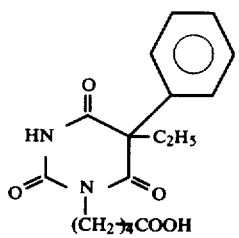

To obtain the acid derivative of primidone following the same Cook et al reference method, 2-thiophenobarbital is alkylated, hydrolyzed, and the product treated with Raney nickel to yield:

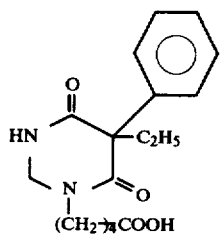

Diphenylhydantoin

Following the method of Cook et al, *Res. Comm. Chem. Path. Pharm.* 5:767(1973), sodium diphenylhydantoin is reacted with methyl 5-bromovalerate followed by acid hydrolysis to yield the following:

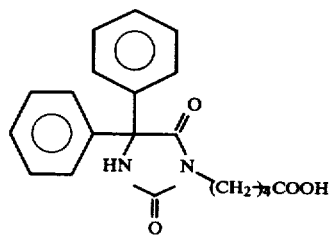

Morphine

Morphine free base is treated with sodium β-chloroacetate according to the method of Spector et al, *Science* 168:1347 (1970) to yield a suitable carboxylic acid derivative.

Nicotine

According to the method of Langone et al, *Biochem.* 12(24):5025(1973), trans-hydroxymethylnicotine and succinic anhydride are reacted to yield the following:

Androgens

Suitable carboxylic acid derivatives of testosterone and androstenedione linked through either the 1- or 7-position on the steroid nucleus are prepared according to the method of Bauminger et al, *J. Steroid Biochem.* 5:739(1974). Following are representative testosterone derivatives:

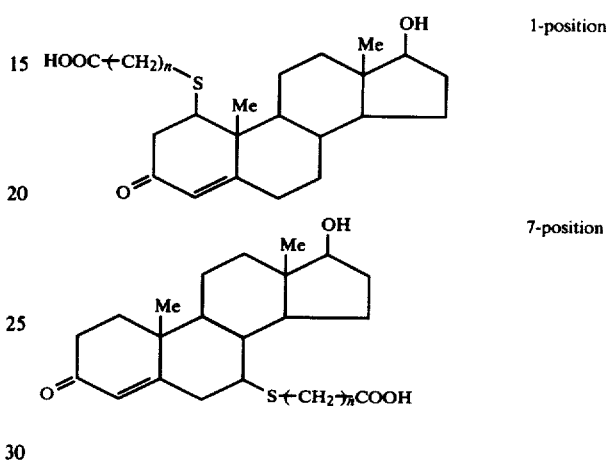

Estrogens

Suitable carboxylic acid derivatives of estrogens, e.g., estrone, estradiol and estriol, are prepared according to the method of Bauminger et al, supra, as represented by the following estrone derivative:

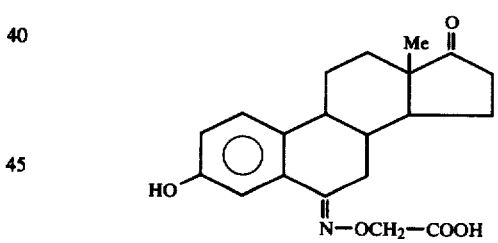

Progesterones

Suitable carboxylic acid derivatives of progesterone and its metabolites linked through any of the 3-, 6- or 7-positions on the steroid nucleus are prepared according to the method of Bauminger et al, supra, as represented by the following progesterone derivatives:

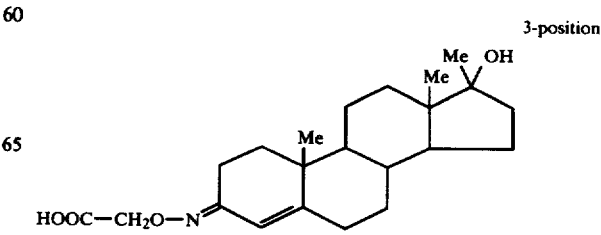

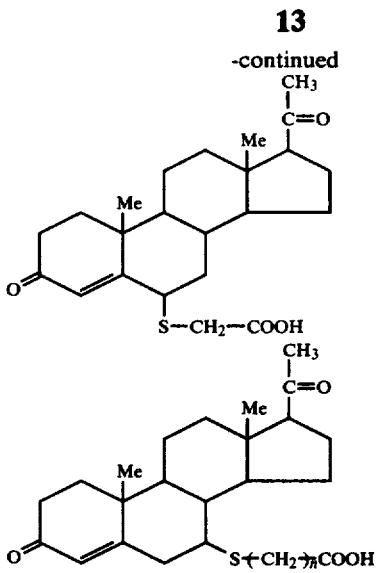

The methods described above are but examples of the many known techniques for forming suitable carboxylic acid derivatives of haptens of analytical interest. The principal derivation techniques are discussed in *Clin. Chem.* 22:726(1976) and include esterification of a primary alcohol with succinic anhydride [Abraham and Grover, *Principles of Competitive Protein-Binding Assays*, ed. Odell and Daughaday, J. B. Lippincott Co. (Philadelphia 1971) pp. 140-157], formation of an oxime from reaction of a ketone group with carboxylmethyl hydroxylamine [*J. Biol. Chem.* 234:1090(1959)], introduction of a carboxyl group into a phenolic residue using chloroacetate [*Science* 168:1347(1970)], and coupling to diazotized p-aminobenzoic acid in the maner described in *J. Biol. Chem.* 235:1051(1960).

The general reaction scheme described above is exemplified by the following descriptions of the synthesis of the ethyl (n=2) and hexyl (n=6) analogs of the FAD-labeled conjugates wherein the ligand is the iodothyronine thyroxine [i.e., +CO)L is of the formula (5) wherein $\beta^1$ and $\beta^2$ are both iodine]. Also provided are descriptions of assay methods, and results therefrom, employing the exemplified analogs as labeled conjugates in a specific binding assay for thyroxine.

1. Ethyl Analog

1-I. PREPARATION OF THE LABELED CONJUGATE 6-(2-Aminoethyl)amino-9-(2',3'-O-isopropylidine-$\beta$-D-ribofuranosyl) purine (2).

13.56 grams (g) [41.5 millimoles (mmol)] of 6-chloro-9-(2',3'-O-isopropylidene-$\beta$-D-ribofuranosyl) purine (1) [Hampton et al, *J. Am. Chem. Soc.* 83:150(1961)] was added with stirring over a 15 minute period to a cold excess of 1,2-diaminoethane [75 milliliters (ml)]. The resulting solution was allowed to stand at room temperature for 24 hours. The solution was evaporated in vacuo and the resulting yellow oil was stirred with 50 ml of cold, saturated sodium bicarbonate. The mixture was evaporated in vacuo and the resulting residue was further repeatedly evaporated in vacuo first from water (3 times from 50 ml) and then from 2-propanol (4 times from 50 ml) to obtain a yellow glass (15 g). A portion (3 g) of the glass was dissolved in a small volume of water which was then applied to the top of a 25 × 55 centimeter (cm) Dowex 50W-X2 cation exchange column in the ammonium form (Bio-Rad Laboratories, Richmond, Calif. USA).

The column was eluted with a linear gradient generated with 2 liters (L) each of water and 0.5 molar (M) ammonium bicarbonate. The elution was completed using a linear gradient generated with 2 L each of 0.5 M and 1 M ammonium bicarbonate. The effluent from the column was collected in 19 ml fractions and monitored by elution on silica gel thin layer chromatography (TLC) plates (E. Merck, Darmstadt, West Germany) with a 9:1 (v:v) mixture of ethanoland ammonium hydroxide. The developed TLC plates were examined under ultraviolet light, then sprayed with ninhydrin reagent [Randerath, *Thin Layer Chromatography*, Academic Press (1966)]. Fractions numbered 250 through 350 from the column chromatography were combined and evaporated in vacuo leaving the desired purine (2) as a pale yellow amorphous glass (1.5 g).

Analysis: Calculated for $C_{15}H_{22}N_6O_4$: C, 51.42; H, 6.33; N, 23.99; Found: C, 50,92; H, 6.54; N, 23.01

NMR (60 MHz, $CDCl_3$): δ1.37 (s,3H, isopropylidene), 1.63 (s,3H, isopropylidene), 5.92 (d, 1H, 1'-ribose), 7.90 (s, 1H, purine), 8.26 (s, 1H, purine)

Optical Rotation $[\alpha]_D^{20} = -74.85°$ (c 1.0, $CH_3OH$)

The remaining crude product (12 g) was purified by chromatography on Dowex 50W-X2 as described above. The overall yield was 8 g (55%).

$\alpha$-(N-Trifluoroacetyl)amino-$\beta$-[3,5-diiodo-4-(3',5'-diiodo-4'-hydroxyphenoxy)phenyl]propanoic acid (4).

This compound was prepared by the method of Blank, *J. Pharm. Sci.* 53:1333(1964). To a cooled (0° C.), stirred suspension of 5 g (6.4 mmol) of L-thyroxine (Sigma Chemical Co., St. Louis, Mo. USA) in 60 ml of dry ethyl acetate was added 11.5 ml of trifluoroacetic acid and 1.9 ml of trifluoroacetic anhydride. After 30 minutes the resulting clear solution was washed three times with 30 ml of water, once with 30 ml of 5% sodium bicarbonate, and twice with 50 ml of saturated sodium chloride. The combined aqueous washings were extracted twice with 20 ml of ethyl acetate. The ethyl acetate layers were combined and washed with 30 ml of water, then dried over magnesium sulfate. The dried ethyl acetate solution was evaporated in vacuo leaving a white solid. Recrystallization from a mixture of ethyl ether and petroleum ether gave a pinkish-white solid (3.95 g, 70.5% yield) having a melting point (m.p.) of 228°-230° C. with decomposition.

Analysis: Calculated for $C_{17}H_{10}F_3I_4NO_5$: C, 23.39; H, 1.15; N, 1.60; Found: C, 23.00; H, 1.05; N, 1.65

NMR [60 MHz, $DCON(CD_3)_2$] δ7.28 (s, 2H, aromatic), 8.03 (s, 2H, aromatic), 9.7 (m, 1H, amido)

IR (KCl): 1700 (>C=O)

Optical Rotation $[\alpha]_D^{25} = -14.97°$ (c 1.0 dimethylsulfoxide)

A second recrystallization produced a second precipitate (0.95 g) m.p. 224°-228° C. with decomposition. The overall yield was 87.5%.

N-{2-[N-(trifluoroacetyl)-3,3',5,5'-tetraiodothyronyl-]aminoethyl}-2',3'-O-isopropylidene adenosine (3).

A solution of 8.72 g (10.0 mmol) of $\alpha$-(N-trifluoroacetyl) amino-$\beta$-[3,5-diiodo-4-(3',5'-diiodo-4'-hydroxyphenoxy)phenyl]propanoic acid (4) and 3.86 g (11.0 mmol) of 6-(2-aminoethyl) amino-9-(2',3'-O-isopropylidene-$\beta$-D-ribofuranosyl) purine (2) in 50 ml of dry dimethylacetamide was prepared under a dry argon atmosphere at −20° C. To this cold stirred solution was added a solution of 3.04 g (11.0 mmol) of diphenylphosphoryl azide (Aldrich Chemical Co., Milwaukee, Wisc. USA) in 10 ml of dry dimethylacetamide followed by the addition of 1.6 ml (11.0 mmol) of dry triethylamine. The solution was left at room temperature for 22 hours. The solution was then added dropwise to 300 ml of cold (0° C.) water with stirring. The resulting white precipitate was collected by filtration and dried in vacuo (56° C.) to give 13.0 g of a light cream colored solid. The solid was dissolved in 500 ml of acetone and the solution was concentrated by boiling. The white solid which precipitated from the boiling acetone solution was collected by filtration while hot. Continued boiling of the filtrate produced two additional precipitates. The three precipitates were combined to give 8 g (66.6% yield) of a white solid, m.p. 198°–200° C. (decomposed).

Analysis: Calculated for $C_{32}H_{30}F_3I_4N_7O_8$: C, 31.89; H, 2.51; N, 8.14; Found: C, 31.95; H, 2.60; N, 7.85

NMR [220 MHz, $(CD_3)_2SO$] δ1.32 (s, 3H, isopropylidene), 1.55 (s, 3H, isopropylidene), 6.14 (d, 1H, 1'-ribose), 7.02 (s, 2H, thyroxine), 7.82 (s, 2H, thyroxine), 8.25 (s, 1H, purine), 8.36 (s, 1H, purine), 8.41 (t, 1H, J=6, amido), 9.64 (d, 1H, J=8, trifluoroacetamido)

Optical Rotation $[\alpha]_D^{25} = -11.82°$ (c 1.0, pyridine)

N-{2-[N-(Trifluoroacetyl)-3,3',5,5'-tetraiodothyronyl]aminoethyl}-2',3'-O-isopropylidene-5'-adenylic acid monotriethylamine salt monohydrate (6).

A solution of 1.2 g (1.0 mmol) of N-{2-[N-(trifluoroacetyl)-3,3',5,5'-tetraiodothyronyl]aminoethyl}-2',3'-O-isopropylidene adenosine (3) in 10 ml of dry triethylphosphate was prepared under a dry argon atmosphere at 0° C. To the cold, stirred solution was added 0.45 ml (5 mmol) of phosphorous oxychloride. The resulting solution was kept for 24 hours at 0° C., then added dropwise with stirring to 1 L of ice water. The resulting precipitate was collected by filtration and dried in vacuo to give 1.23 g of a white solid. The solid was dissolved in acetone and 0.32 ml (2.2 mmol) of triethylamine was added. A precipitate formed. The mixture was evaporated in vacuo and the resulting residue lixiviated with dry acetone, then recrystalized from a mixture of dry methyl alcohol and dry ethyl ether to give 390 mg (27.8% yield) of a white solid, m.p. 173°–183° C. (decomposed).

Analysis: Calculated for $C_{38}H_{48}F_3I_4N_8O_{12}P$: C, 32.50; H, 3.45; N, 7.98; Found: C, 32.24; H, 3.08; N, 7.58

NMR [60 MHz, $(CD_3)_2SO$] δ1.53 (s, 3H, isopropylidene), 6.2 (d, 1H, 1'H-ribose), 7.1 (s, 2H, thyroxine aromatic), 7.87 (s, 2H, thyroxine aromatic), 8.27 (s, 1H, purine), 8.52 (s, 1H, purine)

Optical Rotation $[\alpha]_D^{25} = -17.50°$ (c 1.0, $CH_3OH$)

N-{2-[N-(Trifluoroacetyl)-3,3',5,5'-tetraiodothyronyl]aminoethyl}-5'-adenylic acid (7).

200 milligrams (mg) (0.14 mmol) of N-{2-[N-(trifluoroacetyl-3,3',5,5'-tetraiodothyronyl]aminoethyl}-2',3'-O-isopropylidene-5'-adenylic acid monotriethylamine salt monohydrate (6) was suspended in 1 ml of water (0° C.) and trifluoroacetic acid (9 ml) was added dropwise with stirring. After 30 minutes a clear solution was obtained. The solution was kept cold (0° C.) for an additional 15 hours, then evaporated in vacuo (30° C.). The resulting residue was evaporated four times in vacuo (25° C.) from 20 ml volumes of anhydrous ethyl alcohol and then dried in vacuo (25° C.) leaving a white solid.

The solid was stirred for 30 minutes with 10 ml of cold methyl alcohol, then collected by filtration and dried in vacuo (25° C.) to give a white solid (135 mg, 76% yield) which slowly melted with decomposition above 188° C.

Analysis: Calculated for $C_{29}H_{27}F_3I_4N_7O_{11}P$: C, 27.97; H, 2.19; N, 7.87; Found- C, 28.11; H, 2.31; N, 7.65

NMR [220 MHz, $(CD_3)_2SO$] δ5.95 (d, 1H, 1'-ribose), 7.04 (s, 2H, thyroxine aromatic), 7.84 (s, 2H, thyroxine aromatic), 8.25 (s, 1H, purine), 8.36 (s, 1H, purine), 8.43 (m, 1H, amido), 9.66 (d, 1H, trifluoroacetamido)

Optical Rotation $[\alpha]_D^{25} = -2.72°$ (c 1.0, pyridine)

Flavin adenine dinucleotide - thyroxine conjugate (8).

498 mg (0.4 mmol) of N-{2-[N-(trifluoroacetyl)-3,3',5,5'-tetraiodothyronyl]aminoethyl}-5'-adenylic acid (7) was dissolved in 10 ml of dry dimethylformamide and tri-n-butylamine [96 microliters (μl), 0.4 mmol] was added followed by the addition of 1,1'-carbonyldiimidazole (320 mg, 2.0 mmol). After stirring for 18 hours at room temperature in the absence of moisture, water (280 μl) was added and then the solvent evaporated in vacuo.

The resulting oil was dried by repeated in vacuo evaporation from dry dimethylformamide (4 times from 10 ml). The resulting phosphorimidazolidate was redissolved in 10 ml of dry dimethylformamide and added dropwise to a 0.4 mmol solution of the tri-n-octylamine salt of riboflavin-5'-monophosphate in 10 ml of dry dimethylformamide. The salt was prepared by adding a solution of the ammonium salt of riboflavin-5'-monophosphate (192 mg, 0.4 mmol) in 10 ml of water to a stirred solution of tri-n-octylamine (176 μl, 0.4 mmol) in 100 ml of acetone. After 30 minutes, the resulting mixture was evaporated in vacuo. The residue was dried by repeated evaporation in vacuo from dry dimethylformamide leaving the salt as an orange solid.

The above solution containing the phosphorimidazolidate of (7) and the riboflavin-5'-monophosphate salt was divided into two equal aliquots after 24 hours and one aliquot was evaporated in vacuo. The resulting residue was chromatographed on a column (2.5×78 cm) prepared from 100 g of Sephadex LH-20 (Pharmacia Fine Chemicals, Uppsala, Sweden) which had been preswollen (18 hours) in a 19:1 (v:v) mixture of dimethylformamide and triethylammonium bicarbonate (1 M, pH 7.5). The column was eluted with the above 19:1 (v:v) mixture and 10 ml fractions were collected. The effluent from the column was monitored by elution on silica gel 60 silanised RP-2 TLC places (E. Merck, Darmstadt, West Germany).

The TLC plates were developed using a 40:40:25:1:1 (v:v) mixture of acetone, chloroform, methyl alcohol, water, and triethylamine. Fractions numbered 11 through 17 from the above-mentioned column chromatography were combined and evaporated in vacuo. The residue was chromatographed on a column (2.5×75 cm) prepared from 125 g of Sephadex LH-20 which had been preswollen (18 hours) in 0.3 M ammonium bicarbonate. The column was eluted with 0.3 M ammonium bicarbonate collecting 10 ml fractions. The effluent was monitored by absorption of ultraviolet light at 254 nanometers (nm). The volume of the fractions was increased to 20 ml beginning with fraction number 150. The salt concentration of the eluent was decreased in a stepwise fashion as follows: 0.15 M ammonium bicarbonate at fraction number 295, 0.075 M ammonium bicarbonate at fraction number 376, and water at fraction number 430. A total of 480 fractions was collected. Fractions numbered 200 through 235 were combined and evaporated in vacuo leaving the labeled conjugate (8) as a yellow-orange residue. An alkaline, aqueous solution of this residue exhibited ultraviolet absorption maxima at the following wavelengths: 266 nm, 350 nm, 373 nm, and 450 nm. The yield, estimated from the absorption at 450 was about 5%.

A phosphodiesterase preparation (Worthington Biochemical Corp., Freehold, N.J. USA) isolated from snake venom (*Crotalus Adamanteus*) hydrolyzed the above product to riboflavin-5'-monophosphate and the thyroxine substituted 5'-adenylic acid (7) wherein the trifluoroacetyl blocking group had been removed.

1-II. BINDING ASSAY FOR THYROXINE

The above-prepared labeled conjugate was used in a prosthetic group-labeled specific binding assay as follows (further details regarding such an assay method may be found in the U.S. Patent Application—Ser. No. 917,961—referred to hereinbefore):

A. Preparation of apoglucose oxidase

Purified glucose oxidase with low catalase activity obtained from the Research Products Division of Miles Laboratories, Inc., Elkhart, Ind., USA was twice dialyzed for 12 hours each against 0.5% (w:v) mannitol (30 volumes each). Aliquots of the dialyzate containing 100 mg of glucose oxidase each were lyophilized and stored at $-20°$ C.

Bovine serum albumin (200 mg) was dissolved in 12 ml of water adjusted to pH 1.6 with concentrated sulfuric acid, mixed with 150 mg charcoal (RIA grade from Schwarz-Mann, Orangeburg, N.Y., USA), and cooled to $0°$ C. Lyophilized glucose oxidase (100 mg) was redissolved in 3.1 ml of water and 3 ml was added to the stirred albumin-charcoal suspension with continued stirring for three minutes. The suspension was then filtered through a 0.8 micron, 25 millimeters (mm) diameter Millipore filter (Millipore Corp., Bedford, Mass., USA) mounted in a Sweenex filter apparatus (Millipore Corp.) on a 50 ml disposable plastic syringe. The filtrate was quickly neutralized to pH 7.0 by addition of 2 ml of 0.4 M phosphate buffer (pH 7.6) and thereafter 5 N sodium hydroxide. Dry charcoal (150 mg) was then added and stirred for one hour at $0°$ C. The resulting suspension was filtered first through a 0.8 micron Millipore filter and then through a 0.22 micron Millipore filter. To the filtrate was added glycerol to 25% (v:v) and the stabilized apoglucose oxidase preparation was stored at $4°$ C.

B. Assay Reagents
1. Labeled conjugate—The ethyl analog labeled conjugate prepared as in section 1-I above was diluted in 0.1 M phosphate buffer (pH 7) to a concentration of 1 micromolar ($\mu$M).
2. Apoenzyme—Apoglucose oxidase was diluted with 0.1 M phosphate buffer (pH 7) to a concentration of 0.6 $\mu$M FAD binding sites. The FAD binding site concentration of the apoenzyme preparation was determined experimentally by measuring the minimum amount of FAD required to give maximum glucose oxidase activity when incubated with the apoenzyme.
3. Insolubilized antibody—A washed, moist cake of Sepharose 4B gel (Pharmacia Fine Chemicals, Uppsala, Sweden) activated by cyanogen bromide according to the method of March et al, *Anal. Biochem.* 60:119 (1974) was added to a solution of 85 mg of antibody, (isolated from antiserum against a thyroxine-bovine serum albumin conjugate) in 20 ml of 0.1 M phosphate buffer (pH 7.0) and agitated slowly for 36 hours at $4°$ C. Upon completion of the coupling reaction, 1 ml of 1 M alanine was added and shaking continued for four more hours to block unreacted sites. The resulting Sepharose-bound antibody was washed on a scintered funnel with 400 ml each of 50 mM sodium acetate—500 millimolar (mM) sodium chloride (pH 5) and 50 mM phosphate buffer—500 mM sodium chloride (pH 7), and 800 ml of 100 mM phosphate buffer (pH 7). The moist filter cake was then suspended in 100 mM phosphate buffer (pH 7) containing 0.01% sodium azide to give 22 ml of an about 50% suspension.
4. Standard—A 1.15 mM stock solution of thyroxine in 5 mM sodium hydroxide was diluted to 2 $\mu$M in 0.1 M phosphate buffer (pH 7).
5. Monitoring reagent—A glucose oxidase assay reagent was prepared to contain the following mixture per 130 $\mu$l: 25 $\mu$l of 1.2 mg/ml peroxidase (Sigma Chemical Co., St. Louis, Mo., USA) in 0.1 M phosphate buffer (pH 7), 5 $\mu$l of 10 mM 4-aminoantipyrine in water, 20 $\mu$l of 25 mM 3,5-dichloro-2-hydroxybenzene sulfonate in 0.1 M phosphate buffer (pH 7), 30 $\mu$l of 16.5% bovine serum albumin in 0.1 M phosphate buffer (pH 7), and 50 $\mu$l of 1 M glucose in aqueous saturated benzoic acid solution.

C. Assay Procedure

Binding reaction mixtures were prepared by mixing 150 $\mu$l of the insolubilized antibody suspension, 80 $\mu$l of the labeled conjugate solution, various amounts of the standard thyroxine solution to give varying concentrations of thyroxine in the reaction mixtures, and a sufficient volume of 0.1 M phosphate buffer (pH 7) to make a total volume of 500 $\mu$l. The reaction mixtures were incubated with shaking for two hours at $25°$ C. Each reaction mixture was then vacuum filtered through a glass wool plugged, dry pasteur pipette previously treated sequentially with periodate and ethylene glycol solutions to eliminate possible FAD contamination. To a 300 $\mu$l aliquot of each filtrate was added 130 $\mu$l of the monitoring reagent and 50 $\mu$l of the apoenzyme solution. After one hour, the absorbance of each reaction mixture was measured at 520 nm.

D. Results

Following is Table 3 showing the results of the assay procedure in measuring thyroxine. The absorbance results are expressed as the average of duplicate runs corrected for residual enzyme activity in the apoenzyme solution (absorbance of 0.522) and for endogenous FAD in the antibody suspension (absorbance of 0.142).

TABLE 3

| Volume of Thyroxine Standard Added ($\mu$l) | Absorbance (520 nm) |
| --- | --- |
| 0 | 0.223 |
| 25 | 0.221 |
| 75 | 0.281 |
| 250 | 0.286 |

The results demonstrate that the present labeled conjugates are useful in a specific binding assay method for determining a ligand in a liquid medium.

2. Hexyl Analog

2-I. PREPARATION OF THE LABELED CONJUGATE 6-(6-Aminohexyl)amino-9-(2',3'-O-isopropylidene-β-D-ribofuranosyl) purine (2).

16.0 g (50 mmol) of 6-chloro-9-(2',3'-O-isopropylidene-β-D-ribofuranosyl) purine (1) [Hampton et al, *J. Am. Chem. Soc.* 83:1501 (1961)] was added with stirring to a molten (70° C.) sample of freshly distilled 1,6-diaminohexane (58 g, 500 mmol). The resulting mixture was stirred under argon at 40° C. for 18 hours. The excess diamine was removed by distillation under reduced pressure (60° C., 0.01 mm Hg). The resulting pale yellow residue was adsorbed onto 150 g of silica gel 60 (E. Merck, Darmstadt, West Germany) and used to top a chromatographic 9:1 (v:v) mixture of absolute ethyl alcohol and triethylammonium bicarbonate (pH 7.5, 1 M). The column was eluted with the above 9:1 (v:v) solvent mixture and 900 20 ml fractions were collected. The fractions were examined by thin layer chromatography (TLC) on silica gel 60 eluting with a 7:3 (v:v) mixture of absolute ethyl alcohol and triethylammonium bicarbonate (pH 7.5, 1 M). Fractions numbered 391 through 900 from the column chromatography were combined and evaporated in vacuo leaving 15.0 g of a glassy residue (74% yield). A 1 g sample of the glass was dissolved in a small volume of methyl alcohol and applied to the top of a column prepared from 80 g of Sephadex LH-20 (Pharmacia Fine Chemicals, Uppsala, Sweden) preswollen in methyl alcohol. The column was eluted with methyl alcohol. A total of ninety 8 ml fractions were collected. The fractions were examined by TLC on silica gel 60 eluting with a 7:3 (v:v) mixture of absolute ethyl alcohol and triethylammonium bicarbonate (pH 7.5, 1 M). Fractions numbered 19 through 27 from the column chromatography were combined and evaporated in vacuo leaving 910 mg (91% recovery) of a white glass.

Analysis: Calculated for $C_{19}H_{30}N_6O_4$: C, 56.14; H, 7.44; N, 20.68. Found: C, 53.91; H, 7.33; N, 19.18

NMR (60 MHz, CDCl$_3$): δ1.40 (s, 3H, isopropylidene), 1.63 (s, 3H, isopropylidene) 5.98 (d, 1H, 1'-ribose), 7.92 (s, 1H, purine), 8.36 (s, 1H, purine)

Optical Rotation $[\alpha]_D^{25} = -50.11°$ (c 1.0, methyl alcohol)

N-{6-[N-Trifluoroacetyl)-3,3',5,5'-tetraiodothyronyl]aminohexyl}-2',3'-O-isopropylidene adenosine (3).

A solution of 4.36 g (5.0 mmol) of α-(N-trifluoroacetyl)amino-β-[3,5-diiodo-4-(3',5'-diiodo-4'-hydroxyphenoxy)-phenyl]propanoic acid (4), prepared as described in section 1-I above, and 2.24 g (5.5 mmol) of 6-(6-aminohexyl)amino-9-(2',3'-O-isopropylidene-β-D-ribofuranosyl) purine (2) in 100 ml of dry dimethylformamide was prepared under a dry argon atmosphere at −20° C. To this cold stirred solution was added a solution of 1.52 g (5.5 mmol) of diphenylphosphoryl azide (Aldrich Chemical Co., Milwaukee, Wis., USA) in 50 ml of dry dimethylformamide followed by the addition of 0.8 ml (5.5 mmol) of dry triethylamine. The solution was left at room temperature for 22 hours. The solution was then added dropwise to 600 ml of cold (0° C.) water with stirring. The resulting white precipitate was collected by filtration and dried in vacuo (60° C.) to give 4.90 g (78% yield) of white solid. A sample of this solid was recrystallized from a mixture of acetone and water giving a white solid, m.p. 205°–207° C. (decomposed).

Analysis: Calculated for $C_{36}H_{38}F_3I_4N_7O_8$: C, 34.28; H, 3.04; N, 7.77; Found: C, 34.22; H, 2.99; N, 7.41

Mass Spectrum (20 ma) m/e: 1262 [MH+], 1164 [M+ minus COCF$_3$]

Optical Rotation $[\alpha]_D^{25} = -21.89°$ (c 1.0, pyridine)

N-{6-[N-(Trifluoroacetyl)-3,3',5,5'-tetraiodothyronyl]aminohexyl}-2',3'-O-isopropylidene-5'-adenylic acid monotriethylamine salt monohydrate (6).

A solution of 1.89 g (1.5 mmol) of N-{6-[N-(trifluoroacetyl)-3,3',5,5'-tetraiodothyronyl]aminohexyl}-2',3'-O-isopropylidene adenosine (3) in 15 ml of dry triethylphosphate was prepared under a dry argon atmosphere at −10° C. To the cold stirred solution was added 0.68 ml (7.5 mmol) of phosphorous oxychloride. The resulting solution was kept for 18 hours at −15° C. then added dropwise with stirring to 1.5 L of ice water. The resulting precipitate was collected by filtration and dried in vacuo to give 1.91 g (87% yield) of a white solid. The solid was dissolved in 10 ml methyl alcohol and 0.38 ml (2.6 mmol) of triethylamine was added. This solution was evaporated in vacuo and the resulting residue was recrystallized from a mixture of methyl alcohol and ethyl ether to give 720 mg (33% yield) of a white solid, m.p. 151°–154° C. (decomposed).

Analysis: Calculated for $C_{42}H_{56}F_3I_4N_8O_{12}P$: C, 34.54; H, 3.86; N, 7.67; Found: C, 35.24; H, 3.88; N, 7.75

Mass Spectrum (20 ma) m/e: 1342 [MH+], 1244 [M+ minus COCF$_3$]

Optical Rotation $[\alpha]_D^{25} = -17.20°$ (c 1.0, CH$_3$OH)

N-{6-[N-(Trifluoroacetyl)-3,3',5,5'-tetraiodothyronyl]aminohexyl}-5'-adenylic acid (7).

600 mg (0.41 mmol) of N-{6-[N-(trifluoroacetyl)-3,3',5,5'-tetraiodothyronyl]aminohexyl}-2',3'-O-isopropylidene-5'-adenylic acid monotriethylamine salt monohydrate (6) was suspended in 0.6 ml of water (0° C.) and trifluoroacetic acid (6 ml) was added dropwise with stirring. After 50 minutes a clear solution was obtained. The solution was kept cold (0° C.) for an additional 15 hours then evaporated in vacuo (30° C.). The resulting residue was evaporated in vacuo five times from 20 ml volumes of anhydrous ethyl alcohol then triturated with 30 ml water and washed with a small volume of methyl alcohol. The resulting white solid (430 mg) was recrystallized from methyl alcohol to give 290 mg (54.6% yield) of white solid, m.p. 180°–183° C. (decomposed).

Analysis: Calculated for $C_{33}H_{35}F_3I_4N_7O_{11}P$: C, 30.46; H, 2.71; N, 7.54; Found: C, 30.77; H, 2.55; N, 7.29

Mass Spectrum (20 ma) m/e: 1302 [MH+], 1204 [M+ minus COCF$_3$]

Flavin adenine dinucleotide—thyroxine conjugate (8).

130.13 mg (0.1 mmol) of N-{6-[N-(trifluoroacetyl)-3,3',5,5'-tetraiodothyronyl]aminohexyl}-5'-adenylic acid (7) was placed in an argon atmosphere. To this sample was added a solution of 14 μl (0.1 mmol) of triethylamine in 1 ml of dry dimethylformamide followed by the addition of a solution of 16.2 mg (0.1 mmol) of 1,1'-carbonyldiimidazole in 1 ml of dry dimethylformamide. After 24 hours, a second equivalent of 1,1'-carbonyldiimidazole (16.2 mg) in 1 ml of dry dimethylformamide was added. The above reaction was allowed to proceed a total of 48 hours at room temperature excluding moisture. A sample of 47.3 mg (0.1 mmol) of the ammonium salt of riboflavin-5'-monophosphate was converted to the corresponding tri-n-octylamine salt as described in section 1-I above. This salt was dissolved in 3 ml of dry dimethylformamide and added to the above solution containing the phosphorimidazolidate of the adenylic acid intermediate (7).

The resulting solution was allowed to stand in the dark at room temperature excluding moisture for 24 hours. The solvent was evaporated in vacuo and the resulting residue was chromatographed on a column (2.5×78 cm) prepared from 100 g of Sephadex LH-20 (Pharmacia Fine Chemicals, Uppsala, Sweden) which had been preswollen (18 hours) in a 19:1 (v:v) mixture of dimethylformamide and triethylammonium bicarbonate (1 M, pH 7.5). The column was eluted with the above 19:1 (v:v) mixture and 5 ml fractions were collected. The effluent from the column was monitored by elution on silica gel 60 silanised RP-2 TLC plates (E. Merck, Darmstadt, West Germany). The TLC plates were developed using a 40:40:25:1:1 (v:v) mixture of acetone, chloroform, methyl alcohol, water, and triethylamine.

Fractions numbered 24 through 38 from the column chromatography were combined and evaporated in vacuo. The residue was chromatographed on a column (2.5×85 cm) prepared from 125 g of Sephadex LH-20 which had been preswollen (18 hours) in 0.1 M ammonium bicarbonate. The column was eluted with a linear gradient generated from 2 L of 0.1 M ammonium bicarbonate and 2 L of water and 23 ml fractions collected. The effluent was monitored by ultraviolet absorption (254 nm). Fractions numbered 170 through 182 were combined and evaporated in vacuo. The residue was chromatographed on a column (2.5×55 cm) prepared from 80 g of Sephadex LH-20 which had been preswollen in 0.05 M ammonium bicarbonate. The column was eluted with a linear gradient generated from 2 L of 0.05 M ammonium bicarbonate and 2 L of 0.02 M ammonium bicarbonate. The effluent was monitored by ultraviolet absorption (254 nm). Elution was continued with 2 L of 0.2 M ammonium bicarbonate, collecting 23 ml fractions. A total of 257 fractions was collected. Fractions numbered 70 through 110 were combined and evaporated in vacuo leaving the labeled conjugate (8) as a yellow-orange residue. An alkaline, aqueous solution of this residue exhibited ultraviolet absorption maxima at the following wavelengths: 270 nm, 345 nm, and 450 nm. The yield, estimated from the absorption at 450 nm, was about 5%.

A phosphodiesterase preparation (Worthington Biochemical Corp., Freehold, N.J., USA) isolated from snake venom (*Crotalus Adamanteus*) hydrolyzed the above product to riboflavin-5'-monophosphate and the thyroxine substituted 5'-adenylic acid (7) wherein the trifluoroacetyl blocking group had been removed.

2-II. BINDING ASSAY FOR THYROXINE

The above-prepared labeled conjugate was used in a prosthetic-group labeled specific binding assay as follows (further details regarding such an assay method may be found in the U.S. Patent Application—Ser. No. 917,961-referred to hereinbefore):

A. Preparation of apoglucose oxidase
  The apoenzyme used was prepared by the method described in section 1-II, part A above.
B. Assay Reagents
  1. Labeled conjugate—The hexyl analog labeled conjugate prepared as in section 2-I above this diluted in 0.1 M phosphate buffer (pH 7) to a concentration of 100 nM.
  2. Apoenzyme—This reagent was the same as that described in Section 1-II, part B-2 above.
  3. Insolubilized antibody—This reagent was the same as that described in section 1-II, part B-3 above.
  4. Standard—A 1.15 mM stock solution of thyroxine in 5 mM sodium hydroxide was diluted to 1 µM in 0.1 M phosphate buffer (pH 7).
  5. Monitoring reagent—A glucose oxidase reagent was prepared to contain the following mixture per 117 µl: 25 µl of 1.2 mg/ml peroxidase (Sigma Chemical Co., St. Louis, Mo. USA) in 0.1 M phosphate buffer (pH 7), 5 µl of 10 mM 4-aminoantipyrine in water, 20 µl of 25 mM 3,5-dichloro-2-hydroxybenzene sulfonate in 0.1 M phosphate buffer (pH 7), 17 µl of 30% bovine serum albumin in 0.1 M phosphate buffer (pH 7), and 50 µl of 1 M glucose in aqueous saturated benzoic acid solution.
C. Assay Procedure Binding reaction mixtures were prepared by mixing 30 µl of the insolubilized antibody suspension, 100 µl of the labeled conjugate solution, either 100 µl or none of the standard thyroxine solution, and a sufficient volume of 0.1 M phosphate buffer (pH 7) to make a total volume of 500 µl. The reaction mixtures were incubated with shaking for two hours at 25° C. Each reaction mixture was then vacuum filtered through a glass wool plugged, dry pasteur pipette previously treated sequentially with periodate and ethylene glycol solutions to eliminate possible FAD contamination. To a 350 µl aliquot of each filtrate was added 117 µl of the monitoring reagent and 50 µl of the apoenzyme solution. After one hour, the absorbance of each reaction mixture was measured at 520 nm.

D. Results

Following is Table 4 showing the results of the assay procedure in measuring thyroxine. The absorbance results are expressed as the average of duplicate runs corrected for residual enzyme activity in the apoenzyme solution (absorbance of 0.467) and for endogenous FAD in the antibody suspension (absorbance of 0.041).

TABLE 4

| Volume of Thyroxine Standard Added (µl) | Absorbance (520 nm) |
|---|---|
| 0 | 0.231 |
| 100 | 0.295 |

The results demonstrate that the present labeled conjugates are useful in a specific binding assay method for determining a ligand in a liquid medium.

What is claimed is:

1. In a labeled conjugate for use in specific binding assays of the general formula:
  labeling substance(NH—)—(CO)L wherein —(CO)L is a hapten of molecular weight greater than 100 or an antigenic polypeptide or protein bound to said labeling substance through an amide bond, characterized in that said labeling substance (NH—) has the formula:

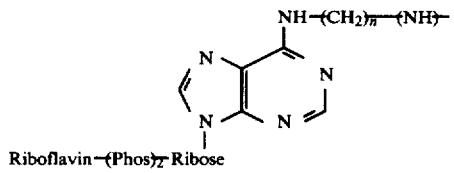

Riboflavin—(Phos)₂—Ribose wherein Riboflavin—(Phos)₂Ribose represents the riboflavin-pyrophosphate-ribose residue in flavin adenine dinucleotide and n=2 through 6.

2. The labeled conjugate of claim 1 wherein —(CO)L is an antigenic polypeptide or protein of molecular between 1,000 and 4,000,000.

3. The labeled conjugate of claim 2 wherein said antigenic polypeptide or protein is an antibody.

4. The labeled conjugate of claim 1 wherein —(CO)L is a hapten of molecular weight between 100 and 1,500.

5. The labeled conjugate of claim 1 wherein —(CO)L is an iodothyronine hormone.

6. The labeled conjugate of claim 5 wherein said iodothyronine hormone is thyroxine.

7. The labeled conjugate of any of claims 1-4 wherein n=2.

8. The labeled conjugate of any of claims 1-4 wherein n=6.

9. A flavin adenine dinucleotide-iodothyronine conjugate of the formula:

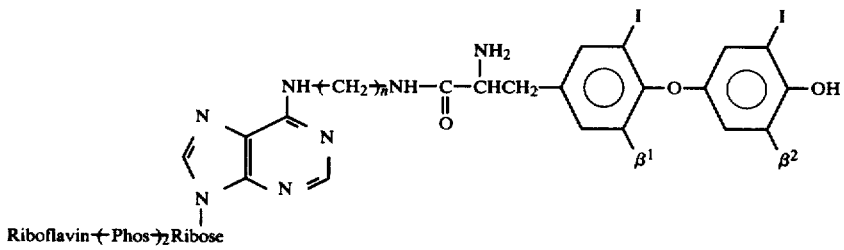

Riboflavin—(Phos)₂Ribose wherein Riboflavin—(Phos)₂—Ribose represents the riboflavin-pyrophosphate-ribose residue in flavin adenine dinucleotide, n=2 through 6, and $\beta^1$ and $\beta^2$ are, independently, hydrogen or iodine.

10. The conjugate of claim 9 wherein n=2.

11. The conjugate of claim 9 wherein n=6.

12. The conjugate of any of claims 9-11 wherein $\beta^1$ and $\beta^2$ are both iodine.

13. The conjugate of any of claims 9-11 wherein $\beta^1$ is iodine and $\beta^2$ is hydrogen.

14. The conjugate of any of claims 9-11 wherein $\beta^1$ is hydrogen and $\beta^2$ is iodine.

15. A flavin adenine dinucleotide-iodothyronine conjugate of the formula:

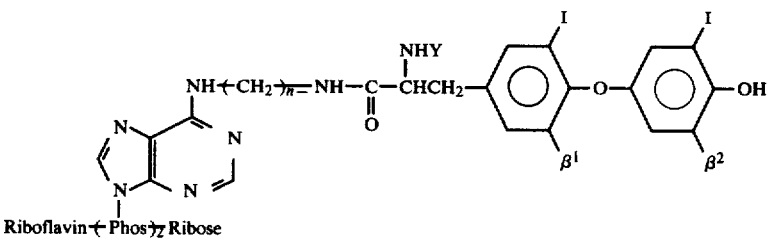

Riboflavin—(Phos)₂Ribose wherein Riboflavin—(Phos)₂Ribose represents the riboflavin-pyrophosphate-ribose residue in flavin adenine dinucleotide, n=2 through 6, Y is trifluoroacetyl, and $\beta^1$ and $\beta^2$ are, independently, hydrogen or iodine.

16. The conjugate of claim 15 wherein n=2.

17. The conjugate of claim 15 wherein n=6.

18. The conjugate of any of claims 15-17 wherein $\beta^1$ and $\beta^2$ are both iodine.

19. The conjugate of any of claims 15-17 wherein $\beta^1$ is iodine and $\beta^2$ is hydrogen.

20. The conjugate of any of claims 15-17 wherein $\beta^1$ is hydrogen and $\beta^2$ is iodine.

21. A compound of the formula

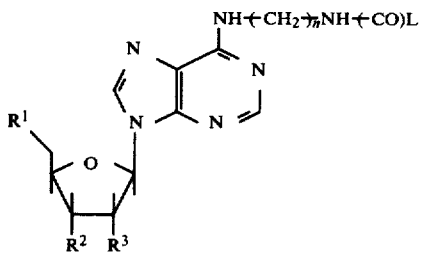

wherein —(CO)L is a hapten of molecular weight greater than 100 or an antigenic polypeptide or protein bound through an amide bond; n=2 through 6; $R^1$ is —OH or

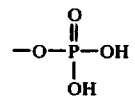

when $R^2$ and $R^3$ together form the group

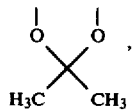

or $R^1$ is

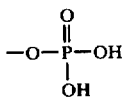

when R² and R³ are —OH.

22. The compound of claim 21 wherein ⁺(CO)L is an antigenic polypeptide or protein of molecular weight between 1,000 and 4,000,000.

23. The compound of claim 22 wherein said antigenic polypeptide or protein is an antibody.

24. The compound of claim 21 wherein ⁺(CO)L is a hapten of molecular weight between 100 and 1,500.

25. The compound of claim 21 wherein ⁺(CO)L is an iodothyronine hormone.

26. The compound of claim 25 wherein said hormone is thyroxine.

27. The compound of any of claims 21 or 22-25 wherein n=2.

28. The compound of any of claims 21 or 22-25 wherein n=6.

29. The compound of claim 21 wherein ⁺(CO)L is

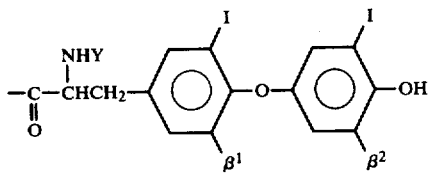

wherein Y is trifluoroacetyl and β¹ and β² are, independently, hydrogen or iodine.

30. The compound of claim 29 wherein n=2.

31. The compound of claim 29 wherein n=6.

32. The compound of any of claims 29-31 wherein both β¹ and β² are iodine.

33. A method for preparing a conjugate of claim 1, which method comprises the steps of:

(a) reacting 6-chloro-9-(2',3'-O-isopropylidine-β-D-ribofuranosyl)purine with an α,ω-diaminopropane, selected from 1,2-diaminoethane, 1,3-diaminopropane, 1,4-diaminobutane, 1,5-diaminopentane, and 1,6-diaminohexane to yield a 6-(ω-aminoalkyl)-9-(2',3'-O-isopropylidine-β-D-ribofuranosyl)purine;

(b) coupling a ligand to be labeled selected from a hapten of molecular weight greater than 100 and an antigenic polypeptide or protein to the primary amino group in said 6-(ω-aminoalkyl)-9-(2',3'-O-isopropylidine-β-D-ribofuranosyl)purine by formation of an amide bond to yield a substituted adenosine intermediate;

(c) treating said substituted adenosine intermediate with phosphorous oxychloride to yield a phosphorylated intermediate;

(d) hydrolyzing said phosphorylated intermediate to remove the isopropylidine group therefrom yielding a 5'-adenylic acid intermediate; and (e) condensing riboflavin-5'-monophosphate with the phosphorimidazolidate formed by treatment of said 5'-adenylic acid intermediate with N,N'-carbonyldiimidazole to yield the desired flavin adenine dinucleotide-labeled conjugate.

34. The method of claim 33 wherein said ligand is an antigenic polypeptide or protein of molecular weight between 1,000 and 4,000,000.

35. The method of claim 33 wherein said antigenic polypeptide or protein is an antibody.

36. The method of claim 33 wherein said ligand is a hapten of molecular weight between 100 and 1,500.

37. The method of claim 33 wherein said ligand is an iodothyronine hormone.

38. The method of claim 37 wherein said hormone is thyroxine.

39. The method of claim 38 wherein the thyroxine is treated to protect the amino group therein prior to coupling step (b) and wherein the protecting group added thereby is removed subsequent to condensing step (e).

40. The method of claim 39 wherein said protecting group is trifluoroacetyl.

41. The method of claim 39 or 40 wherein said α,ω-diaminoalkane is 1,2-diaminoethane.

42. The method of claim 39 or 40 wherein said α,ω-diaminoalkane is 1,6-diaminohexane.

* * * * *